(12) United States Patent
Senni et al.

(10) Patent No.: US 6,559,131 B1
(45) Date of Patent: May 6, 2003

(54) USE OF FUCANE FOR REGULATING THE RECONSTRUCTION OF CONNECTIVE TISSUE

(75) Inventors: Karim Senni, Aulnay sous Bois (FR); Bernard Pellat, Montrouge (FR); Bruno Gogly, Crouy/Ourcq (FR); Catherine Blondin, Paris (FR); Didier Letourneur, Le Plessis Robinson (FR); Jacqueline Jozefonvicz, Lamorlaye (FR); Corinne Sinquin, Nantes (FR); Sylvia Colliec-Jouault, Nantes (FR); Patrick Durand, Reze-les-Nantes (FR)

(73) Assignees: Ifremer, Issy-les-Moulineaux (FR); Centre National de la Recherche Scientifique, Paris Cedex; Universite Rene Descartes, Paris (FR)

(*) Notice: Subject to any disclaimer, the term of this patent is extended or adjusted under 35 U.S.C. 154(b) by 0 days.

(21) Appl. No.: 09/581,810

(22) PCT Filed: Dec. 17, 1998

(86) PCT No.: PCT/FR98/02758

§ 371 (c)(1),
(2), (4) Date: Nov. 6, 2002

(87) PCT Pub. No.: WO99/32099

PCT Pub. Date: Jul. 1, 1999

(30) Foreign Application Priority Data

Dec. 18, 1997 (FR) .............................. 97 16080

(51) Int. Cl.$^7$ .................... A61K 31/715; A61K 31/727
(52) U.S. Cl. ............................ 514/54; 514/56; 514/61; 536/4.1; 536/123; 536/123.1; 536/124; 435/195; 435/200; 435/203
(58) Field of Search ............... 536/4.1, 123, 123.1, 536/124; 514/54, 56, 61; 435/195, 200, 203

(56) References Cited

FOREIGN PATENT DOCUMENTS

| EP | 0 676 207 | 10/1995 |
|---|---|---|
| EP | 0 730 867 | 9/1996 |
| EP | 730 867 | * 9/1996 |
| WO | WO 97/08206 | 3/1997 |

OTHER PUBLICATIONS

Ellouali et al., "Antiproliferative effect and interaction of fucans with cells". Colloids and Surfaces B: Biointerfaces, vol. 2, No. 1–pp. 305–314, 1994.*

Riou et al., "Antitumor and antiproliferative effects of a fucan extracted from Ascophyllum nodosum against a non–small–cell bronchpulmonary carcinoma line." Anticancer Research, 16(3A), 1213–1218, 1996.*

M. Ellouali, et al., Colloids and Surfaces B: Biointerfaces, vol. 2, No. 1–3, pp. 305–314, "Antiproliferative Effect and Interaction of Fucans with Cells", 1994.

D. Logeart, et al., Journal of Biomedical Materials Research, vol. 30, No. 4, pp. 501–508, "Collagen Synthesis by Vascular Smooth Muscle Cells in the Presence of Antiproliferative Polysaccharides", 1996.

* cited by examiner

*Primary Examiner*—Samuel Barts
*Assistant Examiner*—Devesh Khare
(74) *Attorney, Agent, or Firm*—Oblon, Spivak, McClelland, Maier & Neustadt, P.C.

(57) ABSTRACT

The invention concerns the use of fucanes for obtaining medicines for modulating metalloprotease and inhibiting leukocytic elastase. Said medicines help activate collagen synthesis inhibit proliferation of gingival fibroblasts, and activate proliferation of dermal fibroblasts. They are useful in particular for treating periodontal pathologies and dermal lesions.

15 Claims, No Drawings

USE OF FUCANE FOR REGULATING THE RECONSTRUCTION OF CONNECTIVE TISSUE

The invention relates to novel uses of fucans in the context of repairing connective tissue lesions, and in particular for regulating fibroblast functions.

Fibroblasts play an essential role in the equilibrium and repair of connective tissues. They are in particular responsible for renewing extracellular matrix, and in return their functions are modified by the substances present in this matrix.

In particular, in the process of tissue remodelling and healing which intervenes after an injury, the connective tissue is the context for constant exchanges between all the cells involved in this process. These exchanges take place in particular via cytokines or soluble mediators transmitted by the extracellular matrix.

For example, in the covering connective tissues such as the gum and cutaneous tissues, the healing process begins, after the formation of a provisional matrix (red thrombus), with the recruitment of inflammatory cells (leukocytes, macrophages and polynuclear cells), which initiate a phase of destruction of the lesioned tissue.

These inflammatory cells participate in the destruction:
- by secreting matrix proteases such as collagenase (MMP8), leukocytic elastase or cathepsin G,
- by liberating cytokines, and in particular interleukin 1 (IL1), which stimulate the proliferation and migration of fibroblasts and of epithelial cells, and the expression, by these cells, of certain metalloproteases such as interstitial collagenase (MMP1) or gelatinase B (MMP9).

This destruction phase, which begins very soon after the injury, ends when the epithelium and its basement membrane have been reconstituted.

It is prolonged by repair and resolution phases in which the fibroblasts reconstruct and reorganize the collagen framework; the expression by the fibroblasts of gelatinase A (MMP2) is in particular observed, matrix metalloprotease actively participating in all the tissue remodelling phenomena.

Some pathologies are accompanied by a chronic inflammatory state of the connective tissue, in which the balance between the destruction, repair and resolution phases is upset, which leads to defective reconstruction of the lesioned tissue.

This phenomenon is in particular observed in the case of periodontal diseases, or periodontopathies.

The periodontium represents the set of structures (gum, dento-alveolar ligament, alveolar bone and cement) which provides the support for the tooth in its dental alveolus.

Periodontopathies reveal themselves by more or less localized, often recurring, inflammatory episodes of infectious origin at the end of which the periodontal tissue is not correctly reconstructed.

In this pathology, initiation of the inflammatory response and cell proliferation in response to the infectious lesion take place more or less normally. Conversely, the resolution phase is rarely satisfactory; at best repair of the destroyed tissue is observed, but not its complete regeneration, and each episode of the disease induces a tissue loss.

Untreated periodontopathies evolve towards the mobility and then the loss of teeth in adults over forty years of age. Since these periodontal diseases, in a more or less widespread form, concern approximately 10 to 15% of the population, they have considerable consequences in terms of public health.

Currently, most of the treatments proposed are directed towards mechanically unbinding the lesion and reducing the microbial attack by administering antiseptics or antibiotics.

Another therapeutic approach would consist in improving the quality of the repair process to allow it to result in complete regeneration. However, this approach in particular requires being able to stimulate, at the desired moment, the appropriate cell population so as to orient cell proliferations and thus control the processes of tissue modification.

With this aim, the inventors have studied the action of various polysaccharides; it is known that some of these molecules, such as glycosaminoglycans, participate in the composition of the proteoglycans present at the cell/extracellular matrix interface, and play a role in regulating cell functions. It is also known that glycosaminoglycans in a soluble form, for example heparin or dextran derivatives, can modify cell functions via their interaction with various components of the extracellular matrix.

For example, in the case of heparin, a stimulatory effect on cell proliferation was shown in the case of hamster lung fibroblasts, bovine lens epithelial cells [Ulrich et al., Biochem. Biophys. Res. Commun., 139, p. 728–732, (1986)] and capillary endothelial cells [Sudlalter et al., J. Biol. Chem., 264, p. 6892–6897, (1989)].

Conversely, it has also been observed that heparin inhibits the proliferation of certain cell types in a dose-dependent manner; this antiproliferative effect has principally been studied in the case of smooth muscle cells (SMC), for which the inhibition becomes apparent for concentrations of 1 $\mu$g/ml of heparin in the culture media. Heparin opposes both the migration and the proliferation of the SMCs, but does not affect the re-endothelialization or the volume of the connective tissue [Clowes and Clowes, Lab. Invest, 52, p. 611–615, (1985); Clowes and Clowes, Circ. Res., 58, p. 839–845, (1986); Clowes et al., J. Cell. Biol., 107, p. 1939–1945, (1988)].

An inhibition of proliferation has also been observed for other cell types, such as for example sclera fibroblasts [Del Vecchio et al., Invest. Ophtalmol. Vis. Sci., 29, p. 1272–1276, (1988)], 3T3 fibroblasts (mouse embryo fibroblasts which conserve contact inhibition) [Paul et al., Thromb. Res., 18, p. 883–888, (1980)], rat cervix epithelial cells [Lyons-Gioradano et al., Biochem. Biophys. Res. Commun., 148, p. 1264–1269, (1987)] and human dermal fibroblasts.

Ferrao and Mason [Biochem. Biophys. Acta. 1180, 225–230, (1993)] have studied the action of various polysaccharides on human dermal fibroblast proliferation, and indicate that at concentrations of about 100 $\mu$g/ml, heparin, heparan sulphate, pentosan polysulphate and a fucoidan inhibit this proliferation, whereas chondroitin sulphate, dermatan sulphate and hyaluronate have no effect. It is indicated that the inhibitory effect on proliferation leads to a stimulation of type I collagen synthesis. Conversely, an inhibition of collagen I synthesis is observed when the polysaccharides are added to cultures which have reached confluence.

It thus appears that the action of polysaccharides on cell functions is complex and can vary according to the polysaccharide, cell type and tissue concerned, as well as according to the polysaccharide concentration used and the state of the cells.

In the context of research directed towards elucidating the mechanism of action of various polysaccharides on fibroblast functions, and in particular those involved in tissue regeneration, the inventors were in particular interested in fucans.

Fucans are sulphated polysaccharides which participate in the constitution of the cell walls of shoots of brown algae (Pheophyceae); they are also present in some marine animals, such as sea urchins and sea cucumbers. Raw fucan, also termed fucoidan, obtained by acid extraction from the cell walls of brown algae shoots, consists of a heterogeneous population of molecules which comprises principally sulphated L-fucose polymers of high average molar mass (100,000 to 800,000 g/mol).

Fucans have varied biological activities: it has thus been shown that they possess anticoagulant, antithrombotic [T. Nishino and T. Nagumo, Carbohydr. Res. 229, p. 355–362, (1992); Application EP 0403 377; S. Colliec et al. Thromb. Res. 64, p. 143–154 (1991); S. Soeda et al. Thromb. Res. 72, p. 247–256 (1993); Mauray et al. Thromb. Haemost. (5) 1280–1285 (1995)], antiviral [M. Baba et al. J. AIDS, 3, p. 493–499, (1990)], antiangiogenic [R. Hahnenberger and A. M. Jackobson, Glycoconjugate J., 8, 350–353 (1991)] and anticomplementary [C. Blondin et al., Mol. Immunol., 31, p. 247–253, (1994)] activities. It has also been observed that they can act as modulators of cell adhesion [C. G. Glabe et al., J. Cell Sci., 61, p. 475–490, (1983)], of growth factor release [D. A. Belfort et al., J. Cell. Physiol. 157, p. 184–189, (1993)], of proliferation of tumour cells [M. Ellouali et al., Anticancer Res., 13, p. 2011–2020 (1993); D. R. Coombe et al., Int. J. Cancer, 39, pp. 82–90, (1987); D. Riou et al., Anticancer Res., 16, 1213–1218 (1996)] and of vascular smooth muscle cells [Logeart et al., Eur. J. Cell. Biol., 74, pp. 376–384 (1997)], and can block spermatozoid/ovule interactions in various species [M. C. Mahony et al., Contraception, 48, p. 277–289, (1993)].

Preparations of fucans of average molar mass lower than 20,000, or even than 10,000 g/mol, which facilitates their use in a therapeutic context, were obtained, for example, by controlled acid hydrolysis of fucan of high molar mass (Patent EP 0,403,377 in the name of IFREMER), or by radical depolymerization (Application PCT WO/9708206 in the name of IFREMER and CNRS).

In the report which will follow, the term: "fucan" encompasses both the fucans of high molar mass and the preparations of lower molar mass obtained from them.

The inventors have observed that fucans possess a profile of activity on fibroblast functions which is different from that of heparin. They have in particular observed, by testing these two polysaccharides under the same conditions, that whereas heparin inhibits both dermal fibroblast proliferation and that of gum fibroblasts, fucans activate dermal fibroblast proliferation while at the same time inhibiting that of gum fibroblasts. In addition, the inventors have also observed that fucans modify the morphology of dermal fibroblasts which round off, whereas gum fibroblasts, on the contrary, conserve a fibroblastic morphotype.

The inventors have also observed that fucans increase the amount of proteins in the cell layer and the activity of MMP2 (gelatinase A), and inhibit leukocytic elastase.

These effects reveal themselves both on dermal fibroblasts and on gum fibroblasts.

A subject of the present invention is the use of a fucan for obtaining a medicinal product which modifies the expression and/or the activity of fibro-blastic metalloproteinases, and in particular of MMP2, and which inhibits leukocytic elastase.

Fucans thus make it possible to control proteolytic activity in connective tissues such as dermal and gum tissues, and in particular to limit elastase activity, which exhibits considerable destructive potential with respect to connective macromolecular structures, while at the same time on the contrary promoting the activity of proteases which participate in tissue reconstruction, such as MMP2.

According to a preferred embodiment of the present invention, said medicinal product can also be used to inhibit the proliferation of gum fibroblasts and to activate their collagen synthesis. It allows the treatment of periodontal pathologies via an improvement in the resolution phase.

Specifically, due to the combination of a regulation of proteolytic activities (in particular activation of MMP2 and inhibition of elastase) with an inhibition of gum fibroblast proliferation, an increase in the synthesis of a physiological matrix, and the conservation of the fibroblastic morphotype, fucans make it possible to engage these gum fibroblasts in the remodelling pathway which is required for any process of tissue repair or regeneration.

According to another embodiment of the present invention, said medicinal product can also be used to activate the proliferation of dermal fibroblasts and their collagen synthesis. It thus allows the treatment of dermal lesions by improving the recovery phase of the lesioned tissue.

The medicinal products obtained in accordance with the invention can be administered generally (orally or parenterally). They can also be administered locally, in the form of gels, creams, ointments, lotions, lozenges, mouthwashes, etc.

They can also be administered in situ via substrates, resorbable or nonresorbable devices such as for example delayed-release supports, or slowly-disintegrating sponges.

Fucans can also be used in cosmetology, as fibroblast proliferation activators in the context of treatments aimed at aesthetics, for example of antiwrinkle treatments or of prevention of skin ageing, etc.

The present invention will be better understood with the aid of the further description which will follow, which refers to examples demonstrating the activity of fucans on dermal and gum fibroblasts.

EXAMPLE 1

ACTION OF FUCAN ON THE PROLIFERATION OF GUM AND DERMAL FIBROBLASTS

Polysaccharides

Fucan:

The fucan used is a fraction of average molar mass 20,000±2000 obtained from the marine brown algae Ascophylum nodosum, according to the method described in patent EP 0,403,377. This fucan has a high fucose level (44±5%), few uronic acids (7±3%), 28±3% of sulphate groups and no proteins.

Cells

The fibroblasts used were obtained from explants of healthy gum and dermal tissues originating from three different donors (from 15 to 30 years old).

Culture

The culture protocol is the same for the gum fibroblasts and the dermal fibroblasts.

From the explant, the cells are cultured in a DMEM (Dulbecco's Modified Eagle Medium) culture medium containing D-glucose at 1 g/l and GLUTAMAX at 0.862 g/l, an antibiotic (penicillin/streptomycin at 1000 U/ml), fungizone (amphotericin B at 250 U/ml; GIBCO BRL) and 20% foetal calf serum (FCS).

The specimens are removed from the transport medium. Having been rinsed three times in the culture medium, they are finely cut up into small pieces of 1 $mm^2$ approximately. They are arranged so that the epithelial layer is oriented upwards and the connective layer is oriented downwards, in contact with the 25 $cm^2$ culture dish. The dish is placed vertically in an incubator at 37° C. (95% air, 5% $CO_2$) for half an hour, so as to promote adhesion.

After adding a drop of medium onto each tissue fragment, the dish is returned to the incubator overnight.

The following day, the culture medium is replaced with fresh medium. The dish is left like this in the incubator for four days.

The medium is then changed every three days, and the explants are removed as soon as the fibroblasts adhere to the wall. When the fibroblasts have invaded the entire bottom of the dish, the primary culture is terminated.

Subsequent Passages

The culture medium is removed, and the dish is rinsed three times with DPBS (Dulbecco's Phosphate Buffer Saline) to remove all trace of FCS and then trypsinized (trypsine diluted to 0.05% in DPBS and filtered). After 5 minutes, the fibroblasts detach and round off.

The cells are distributed into 3 dishes, in DMEM (10 to 12 ml) containing 10% of FCS and 1000 U/ml of penicillin/streptomycin.

The medium is changed regularly until complete colonization of the new dish.

Cell Proliferation Protocol.

The confluent cells are trypisinized, suspended in DMEM in a proportion of 7000 to 10,000 cells/ml, and then distributed into the wells of 24-well plates. Medium containing 10% of FCS is added to the wells, and the seeded plates are returned to the incubator for two hours to allow adhesion. Three hours after the seeding, the media are replaced with a DMEM/10% FCS medium (control group) or a DMEM/10% FCS medium with 1, 10 or 100 $\mu$g/ml of the tested polysaccharide (fucan or heparin). The cells are counted each day until the $4^{th}$ day.

The proliferation percentage is calculated using the relationship:

%p=(net proliferation with product−1)×100 net proliferation of controls.

If the calculated value is positive, there is cell proliferation; if it is negative, there is inhibition of cell proliferation.

The results concerning the proliferation percentage in the presence of various fucan concentrations are illustrated by Tables Ia (gum fibroblasts) and Ib (dermal fibroblasts) below:

TABLE Ia

| Fucan concentration Days | 1 $\mu$g/ml | 10 $\mu$g/ml | 100 $\mu$g/ml |
|---|---|---|---|
| 1 | −6 | −6 | −6 |
| 2 | −9 | −36 | −32 |
| 3 | −11 | −41 | −44 |
| 4 | −22 | −39 | −55 |

TABLE Ib

| Fucan concentration Days | 1 $\mu$g/ml | 10 $\mu$g/ml | 100 $\mu$g/ml |
|---|---|---|---|
| 1 | 14 | 41 | 14 |
| 2 | 13 | 43 | 11 |
| 3 | 17 | 46 | 21 |
| 4 | 37 | 56 | 41 |

These results show that fucan influences the proliferation of gum fibroblasts and of dermal fibroblasts differently:

Gum fibroblasts (Table Ia): an inhibition of proliferation which reaches its maximum in the exponential growth phase can be observed. This inhibition appears to be dose-dependent.

Dermal fibroblasts (Table Ib): the various experiments show a proproliferative effect of fucan on the dermal fibroblast cultures. This effect is maximal on the $4^{th}$ day of culture, and 10 $\mu$g/ml is the most effective concentration.

EXAMPLE 2

INFLUENCE OF FUCAN ON MMP2 (GELATINASE A) ACTIVITY AND ON FIBROBLAST MORPHOLOGY

The cells are seeded in 24-well plates (7000 to 10,000 cells/ml) and cultured in the presence of DMEM/10% FCS. At confluence, the medium is replaced with DMEM for the controls, or DMEM containing the various fucan concentrations (1, 10 or 100 $\mu$g/ml), for 24 hours. The media are then recovered, for detecting the gelatinolytic activity of pro-MMP2, and the cells, which are fixed and stained (methanol/GIEMSA) are counted and morphometrically analysed in a BIOCOM 200 computer.

Determination of Gelatinolytic Activity

The gelatinolytic activities present in the culture media are detected by zymography, after electrophoresis under nonreducing conditions in SDS-polyacrylamide gel+gelatin, and then removal of the SDS.

The results are quantified by semiautomatic image analysis on a BIOCOM 200 computer. For each band which appears on the gel, the product of the grey density (D) is determined by the surface area of the band (S). This product, reported to cell number, makes it possible to assess and to compare the various gelatinolytic activities.

The results are illustrated by Table II below:

TABLE II

| | D × S for 1000 cells | | Indexed variations | |
|---|---|---|---|---|
| | Dermal fibroblasts | Gum fibroblasts | DF | GF |
| Controls | 16669 ± 5563 | 16453 ± 5066 | 100 | 100 |
| 1 $\mu$g/ml | 36652 ± 6829 | 21450 ± 2880 | 219 | 130 |
| 10 $\mu$g/ml | 25316 ± 3030 | 25816 ± 2304 | 151 | 157 |
| 100 $\mu$g/ml | 27613 ± 5710 | 22656 ± 5656 | 165 | 137 |

These results show that fucan significantly increases, from the lowest concentrations, the secretion of pro-MMP2 in both fibroblast types studied.

Cellular Morphometry

Four parameters are studied: the circumference (expressed in $\mu$m), the surface area of the cell (expressed in $\mu$m$^2$), its equivalent diameter (expressed in $\mu$m) and its shape factor.

The equivalent diameter is the diameter of the smallest circle which completely contains the cell. It defines the greatest length of the cell.

The shape factor is determined by the ratio $4\pi S/C^2$, where S represents the surface area and C the circumference; when it approaches zero, it indicates an elongated structure; when it increases, it indicates a rounding off of the shape.

The results are illustrated by Tables IIIa (gum fibroblasts) and IIIb (dermal fibroblasts) below:

TABLE IIIa

| | Circumference | Surface area | Diameter | Shape factor |
|---|---|---|---|---|
| Controls | 1050 ± 234 | 6942 ± 1682 | 93 ± 11 | 0.08 |
| 1 $\mu$g/ml | 1039 ± 180 | 6154 ± 1396 | 87 ± 10 | 0.07 |
| 10 $\mu$g/ml | 1182 ± 209 | 5203 ± 1389 | 82 ± 10 | 0.04 |
| 100 $\mu$g/ml | 910 ± 111 | 4753 ± 1036 | 77 ± 9 | 0.07 |

TABLE IIIb

|  | Circumference | Surface area | Diameter | Shape factor |
|---|---|---|---|---|
| Controls | 924 ± 154 | 5446 ± 1241 | 82 ± 9 | 0.08 |
| 1 µg/ml | 878 ± 125 | 5665 ± 807 | 84 ± 6 | 0.11 |
| 10 µg/ml | 919 ± 136 | 6770 ± 889 | 92 ± 6 | 0.13 |
| 100 µg/ml | 851 ± 89 | 7556 ± 1580 | 97 ± 10 | 0.13 |

These results show that gum and dermal fibroblasts react differently to fucan:

Gum fibroblasts: the surface area and the diameter of the cells decrease, whereas their circumference increases. These parameters make it possible to calculate a shape factor approaching zero, which implies an elongated cell of fibroblastic type.

Dermal fibroblasts: under the influence of fucan, the surface area and diameter of the cells increases, whereas their circumference remains constant. The shape factor increases, which implies cells which are rounding off.

EXAMPLE 3

INFLUENCE OF FUCAN ON LEUKOCYTIC ELASTASE ACTIVITY

Leukocytic elastase activity in the presence of fucan (1 µg/ml or 10 µg/ml) or of heparin H108 (1 IU/ml or 10 IU/ml) is measured using as substrate the synthetic peptide:

N-MeO-Succ-Ala-Ala-Pro-Val-PA (SEO ID NO: 1) according to the protocol described by Bizot-Foulon et al. [International Journal of Cosmetic Science, 17, p. 255–264, (1995)].

TABLE IV

| FUCAN | | HEPARIN | |
|---|---|---|---|
| Concentration | % inhibition | Concentration | % inhibition |
| 1 µg/ml | 51.8 | 1 IU/ml | 16.95 |
| 10 µg/ml | 54.5 | 10 IU/ml* | 9.25 |

1 IU/ml = 5.8 µg/ml

These results show that in the case of heparin, leukocytic elastase inhibition is limited, and that the inhibitory effect decreases when the heparin concentration increases; on the contrary, in the case of fucan, the inhibition is much greater, from the 1 µg/ml concentration.

EXAMPLE 4

INFLUENCE OF FUCAN ON FIBRILLAR COLLAGEN BIOSYNTHESIS

Collagen biosynthesis is measured after incorporation of tritiated proline ($^3$H-Pro).

The cells are cultured in DMEM/10% FCS until confluence. The media are then replaced with DMEM containing ascorbic acid (50 µg/ml) and $^3$H—Pro (25 µCi/ml) for the controls, or the same medium with fucan added at various concentrations (1, 10 or 100 µg/ml) or with heparin H108 added at a concentration of 400 µg/ml. After 24 hours, the media and the cell layer are recovered.

The specific extraction of proline and hydroxyproline radiolabelled by the method of Rojkind and Gonzales [Anal. Biochem. 57:1–7 (1974)] makes it possible to determine the total collagen synthesis/total protein synthesis ratio.

The results are illustrated by Tables Va (gum fibroblasts) and Vb (dermal fibroblasts) below:

TABLE Va

|  | Collagen synthesis/ protein synthesis | % of collagens present in the cell layer | % of proteins present in the cell layer |
|---|---|---|---|
| Controls | 5 | 29 | 34 |
| 1 µg | 5 | 26 | 38 |
| 10 µg | 5 | 38 | 44 |
| 100 µg | 5 | 40 | 51 |

TABLE Vb

|  | Collagen synthesis/ protein synthesis | % of collagens present in the cell layer | % of proteins present in the cell layer |
|---|---|---|---|
| Controls | 7 | 33 | 43 |
| 1 µg | 5 | 38 | 55 |
| 10 µg | 4.5 | 38 | 55 |
| 100 µg | 5 | 32 | 63 |

These results show that, under the effect of fucan, both types of fibroblast tend to synthesize a matrix which is preferentially deposited in the cell layer. This matrix deposit appears to concern all proteins, and not only collagen, which, for both cell types, excludes any fibrotic risk.

Gum fibroblasts: the overall collagen synthesis/overall protein synthesis ratio does not vary. The percentage of collagens in the cell layer increases in parallel with the percentage of proteins, in a dose-dependent manner.

Dermal fibroblasts: the percentage of collagens present in the cell layer (intra-+pericellular) increases at low dose and does not vary at 100 µg/ml, whereas the amount of proteins present in this compartment increases with the fucan concentration. The overall collagen synthesis/overall protein synthesis ratio decreases.

Influence of fucan or of heparin on the deposit of pericellular collagens synthesized by gum fibroblasts.

The cells are cultured as described above, in the presence of tritiated proline; fucan at a concentration of 100 µg/ml, or heparin H108 (average molar mass 21,000±2000, activity of 173 IU/mg, sold by Choay Sanofi) at a concentration of 400 µg/ml is added.

To estimate the amount of fibrillar collagen, the intracellular and pericellular collagens are differentially extracted with deoxycholate (which extracts essentially intracellular procollagen) and SDS (which solubilizes pericellular collagen accumulated in the extracellular matrix).

The results are illustrated by Table VI below:

TABLE VI

|  | % pericellular collagen | Variation/controls |
|---|---|---|
| Controls | 19 | 0 |
| H108 | 29 | +35 |
| Fucan | 44 | +56 |

These results make it possible to confirm that the increase in collagens in the cell layer is indeed due to a matrix deposit (thus pericellular), and not to excessive intracellular retention. They also show that this matrix deposit is more considerable in the presence of fucan than in the presence of heparin.

What is claimed is:

1. A method for repairing a connective tissue lesion comprising:
contacting a tissue in need of repair with at least one fucan.

2. The method of claim 1, wherein said fucan increases the expression and/or the activity of a fibroblastic metalloproteinase or that inhibits leukocyte elastase, or both.

3. The method of claim 1, comprising contacting said tissue with a fucan that increases the expression and/or the activity of the metalloproteinase MMP2 (gelatinase A).

4. The method of claim 1, wherein said fucan inhibits leukocyte elastase.

5. The method of claim 1, wherein said fucan increases deposition of a matrix comprising collagen and other proteins in the cell layer of dermal fibroblasts without increasing collagen expression.

6. The method of claim 1, wherein said fucan increases the proliferation of dermal fibroblasts.

7. The method of claim 1, wherein said fucan has an average molecular mass of 20,000±2000.

8. The method of claim 1, wherein said fucan is obtained from marine brown algae.

9. A method for treating a periodontal pathology or a dermal pathology comprising contacting a periodontal tissue or a dermal or connective tissue with at least one fucan that increases the expression and/or the activity of a fibroblastic metalloproteinase or that inhibits leukocyte elastase, or both.

10. The method of claim 9, comprising contacting said tissue with a fucan that increases the expression and/or the activity of the metalloproteinase MMP2 (gelatinase A).

11. The method of claim 9, wherein said fucan inhibits leukocyte elastase.

12. The method of claim 9, wherein said fucan increases deposition of a matrix comprising collagen in the cell layer of gum fibroblasts without increasing collagen expression.

13. The method of claim 9, wherein said fucan decreases proliferation of gum fibroblasts.

14. The method of claim 9, wherein said fucan has an average molecular mass of 20,000±2000.

15. The method of claim 9, wherein said fucan is obtained from marine brown algae.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N-MeO-Succ-
<220> FEATURE:
<221> NAME/KEY: MOD_RES
<222> LOCATION: (4)..(4)
<223> OTHER INFORMATION: -PA

<400> SEQUENCE: 1

Ala Ala Pro Val
1